United States Patent [19]

Minagawa et al.

[11] 4,173,599

[45] Nov. 6, 1979

[54] 2,2,6,6-TETRAALKYL-4-PIPERIDYL KETONES AND KETALS AS STABILIZERS FOR SYNTHETIC POLYMERS

[75] Inventors: Motonobu Minagawa, Kosigaya; Naohiro Kubota; Toshihiro Shibata, both of Urawa, all of Japan

[73] Assignee: Argus Chemical Corporation, Brooklyn, N.Y.

[21] Appl. No.: 886,965

[22] Filed: Mar. 16, 1978

[30] Foreign Application Priority Data

Mar. 31, 1977 [JP] Japan .................. 52-37051

[51] Int. Cl.$^2$ .................. C07D 491/10; C07D 491/20; C08K 5/35
[52] U.S. Cl. .................. 525/66; 260/23 XA; 260/45.8 N; 260/45.8 NZ; 260/45.85 B; 546/19; 525/243; 525/256
[58] Field of Search .................. 260/45.8 NZ, 293.63, 260/293.66, 880 R

[56] References Cited

U.S. PATENT DOCUMENTS

| | | | |
|---|---|---|---|
| 3,839,273 | 10/1974 | Murayama et al. | 260/293.66 |
| 3,940,363 | 2/1976 | Murayama et al. | 260/45.8 NZ |
| 4,007,158 | 2/1977 | Murayama et al. | 260/45.8 NZ |
| 4,016,168 | 4/1977 | Murayama et al. | 260/293.63 |

Primary Examiner—Donald E. Czaja
Assistant Examiner—R. A. White

[57] ABSTRACT

2,2,6,6-tetraalkyl-4-piperidyl ketones and ketals are provided, useful as stabilizers for organic polymeric materials, and having the general formula:

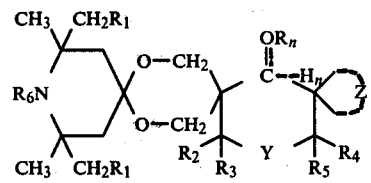

wherein n are each 0 or 1 and are each the same;
R is selected from the group consisting of hydrogen, alkyl having from one to about eighteen carbon atoms, and acryl

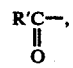

R' being alkyl having from one to about eighteen carbon atoms;
$R_1$, $R_2$, $R_3$, $R_4$ and $R_5$ are selected from the group consisting of hydrogen and alkyl having from one to about eighteen carbon atoms;
$R_6$ is selected from the group consisting of hydrogen and O-;
Y is selected from the group consisting of a carbon-to-carbon bond—, oxy —O—; alkylene having from one to about three carbon atoms, and alkyl-substituted alkylene, the alkylene having from one to about three carbon atoms, the alkyl having from one to about six carbon atoms; and
Z is selected from the group consisting of:

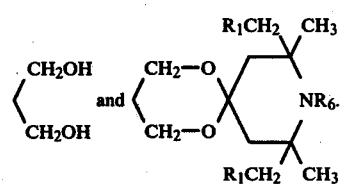

29 Claims, No Drawings

2,2,6,6-TETRAALKYL-4-PIPERIDYL KETONES AND KETALS AS STABILIZERS FOR SYNTHETIC POLYMERS

Hindered 2,2,6,6-tetraalkyl-4-carboxylic acid ester piperidine compounds have been proposed by Murayama et al U.S. Pat. No. 3,640,928 patented Feb. 8, 1972 as light and heat stabilizers for synthetic polymers, such as polyolefins, polyvinyl chloride, polyvinylidene chloride, polyurethanes, and polyamides. These compounds have the general formula:

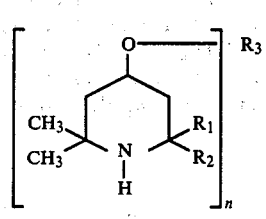

or a salt thereof.

In the above formula:
$R_1$ and $R_2$ which may be the same or different, each are an alkyl group such as methyl, ethyl, isopropyl or dodecyl, or they form, together with the carbon atom to which they are attached, a saturated alicyclic group such as:

or a group of the formula

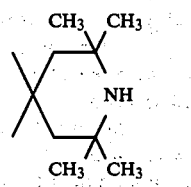

n is an integer of 1 to 3 inclusive; and
$R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al patent has been followed by a large number of patent and literature disclosures by Murayama et al and others of compounds including a 2,2,6,6-tetrasubstituted-4-piperidyl group attached to a base molecule of varying structures.

Murayama et al U.S. Pat. No. 3,898,303 patented Aug. 5, 1975 propose piperidino-spiro-hydantoin derivatives having the formula:

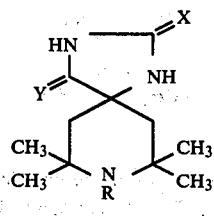

wherein
R represents an alkyl group, an alkenyl group, an alkenoyl group which may be substituted with an aryl group, a hydroxyalkyl group, an alkoxyalkyl group, an alkoxycarbonylalkyl group, an acyloxyalkyl group, a cyanoalkyl group or nitroso group, and X and Y individually represent oxygen atom or sulfur atom.

Murayama et al in U.S. Pat. No. 3,899,464 patented Aug. 12, 1975 disclose a variation of the piperidino spiro compounds having the formula:

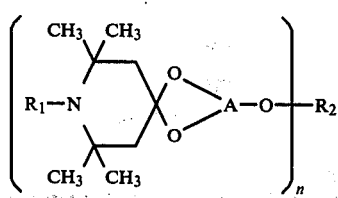

wherein
$R_1$ represents hydrogen atom, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, n is an integer of 1 to 4;

when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, N-substituted carbamoyl group, a N-substituted thiocarbamoyl group, a monovalent group from an oxoacid or group

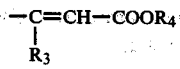

in which
$R_3$ represents hydrogen atom, a lower alkyl group or phenyl group and $R_4$ represents an alkyl group;

when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid;

when n is 3, $R_2$ represents an aromatic triacyl group or a trivalent group from an oxoacid; and when n is 4, $R_2$ represents an aromatic tetraacyl group, and A represents a group

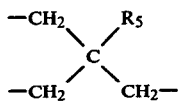

in which
R₅ represents hydrogen atom or a lower alkyl group or, when n is 1, R₅ may represent together with R₂ a group

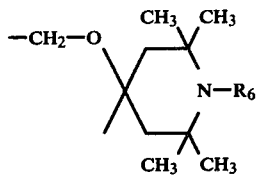

in which
R₆ represents the same group as defined in R₁ and may be the same or different from R₁, or a group

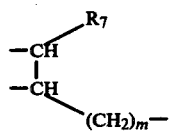

in which
m is 1 or 2 and R₇ represents hydrogen atom or, when n and m are 1, R₇ represents methylene group together with R₂.

Murayama et al U.S. Pat. No. 3,840,494, patented Oct. 8, 1974 provides acid esters of 4-piperidinol derivatives having the formula:

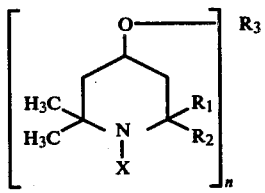

wherein
R₁ and R₂ may be the same or different and represent an alkyl group of one to four carbon atoms or they may form, together with the carbon atom to which they are attached, a saturated alicyclic group or the group of the formula:

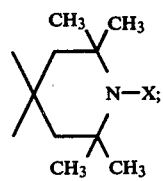

X is hydrogen atom, oxygen free radical (—O·) or an alkyl group of one to four carbon atoms;
n is an integer of 1 through 4 inclusive; and R₃ represents,
when n is 1, an acyl group derived from an aliphatic or aromatic monocarboxylic acid,
when n is 2, a diacyl group derived from an aliphatic or aromatic dicarboxylic acid or carbonyl group,
when n is 3, a triacyl group derived from an aliphatic or aromatic tricarboxylic acid or a trivalent group obtained by eliminating three hydroxyl groups from phosphoric acid, phosphorous acid or boric acid, and
when n is 4, a tetraacyl group derived from an aromatic tetracarboxylic acid or a tetravalent group obtained by eliminating four hydroxyl groups from orthosilicic acid.

Murayama et al U.S. Pat. No. 3,933,735 patented Jan. 20, 1976 propose 4-piperidone derivatives having a structure similar to the 4-piperidyl derivatives, but with a keto oxygen at the 4-position of the piperidine ring.

Murayama et al U.S. Pat. No. 3,941,744 patented Mar. 2, 1976, disclose another variation of the piperidino spiro derivatives having the formula:

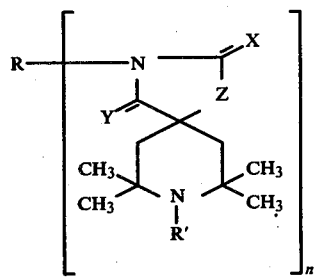

wherein
R′ represents an alkyl group, a substituted alkyl group, an acyl group, an alkoxycarbonyl group, a substituted alkoxycarbonyl group, an amino group, a substituted amino group or nitroso group;
X represents oxygen atom or sulfur atom;
Y represents oxygen atom, sulfur atom or a group of the formula =N—R″ in which R″ is hydrogen atom, an alkyl group or a substituted alkyl group;
Z represents oxygen atom or a group of the formula >N—R‴ is hydrogen atom, an alkyl group or a substituted alkyl group;
n is an integer of 1 through 4 inclusive; and
R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group; when n is 2, an alkylene group, an alkenylene group, an arylene group, a substituted arylene group, an aralkylene group, an alkylenediphenylene group, a bis-(acyloxyalkylene) group, an alkylene-bis-(oxycarbonylalkyl) group, a dialkylene ether group or a diphenylene ether group; when n is 3, an alkanetriyl group, a tris-(acyloxyalkylene) group, an alkane-tris-(oxycarbonylalkyl) group or a group of the group

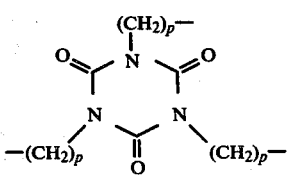

in which p is an integer of 1 through 8 inclusive; and when n is 4, an alkane tetrayl group, a tetrakis-(acyloxyalkylene) group or an alkanetetrakis(oxycarbonylalkyl) group.

Murayama et al U.S. Pat. No. 3,940,363 patented Feb. 24, 1976 disclose a further variation in which two 2,2,6,6-tetrasubstituted-4-piperidyl groups are linked together via the ring nitrogen atom to an R' alkylene linking group, which may be interrupted with an oxygen or sulfur atom, an alkenylene group, an alkynylene group, an aralkylene group, an aliphatic diacyl group, a group having the formula:

$$-(CH_2)_n-O-\overset{O}{\underset{\|}{C}}-X-\overset{O}{\underset{\|}{C}}-O-(CH_2)_n-$$

in which
n is an integer of 1 or 2 and X is an alkylene group, or o-, m- or p-phenylene group or the carbon atoms of CO groups may be directly joined in the absence of X or a group of the formula:

$$-CH_2-\overset{O}{\underset{\|}{C}}-O-Y-O-\overset{O}{\underset{\|}{C}}-CH_2-$$

in which
Y is an alkylene group or o-, m- or p-phenylene group.

Ramey et al U.S. Pat. Nos. 3,875,169 patented Apr. 1, 1975 and 3,991,012 patented Nov. 9, 1976 provide bicyclic hindered amines of the formula:

[structure: bicyclic hindered amine with CH3, CH3, NX, CH3, CH3 substituents and H OC(=O)—R group, subscript n]

wherein
X is H, O, or OH,
n is 1 or 2, and
(a) when n is 1, R is straight-or branched-chain alkyl having one to twenty carbon atoms, phenyl or phenyl substituted by one or more lower alkyl groups, and
(b) when n is 2, R is straight- or branched-chain alkylene having one to twenty carbon atoms, phenylene or phenylene substituted by one or more lower alkyl groups.

Preferred compounds of formula I are those wherein X is H or O; and n is 1 or 2, and
(a) when n is 1, R is n-alkyl having one to twenty atoms, and
(b) when n is 2, R is n-alkylene having one to twelve carbon atoms.

Ramey et al U.S. Pat. Nos. 3,907,803 patented Sept. 23, 1975 and 4,001,181 patented Jan. 4, 1977 provide hindered piperidine carboxamide acids and metal salts thereof of the formula:

[structure: piperidine with CH3, CH3, CH3, CH3 substituents, $R_3$—N, $R_1$, $R_2$, linked via —N(H)—C(=O)—$R_4$—C(=O)—O—M, subscript z]

wherein
$R_1$ and $R_2$ independently of each other are straight- or branched-chain lower alkyl having one to six carbon atoms, or together with the carbon to which they are bound form a cyclopentyl or cyclohexyl ring, which is unsubstituted or substituted with a methyl group,
$R_3$ is hydrogen, alkyl having one to twelve carbon atoms, β-methoxyethyl alkenyl having three or four carbon atoms, propargyl, benzyl, or alkyl-substituted benzyl,
$R_4$ is straight- or branched-chain alkylene having one to eight carbon atoms, phenylene, phenylene substituted with one or more alkyl groups, or the group —$(CH_2)_m Y(CH_2)_n$—, wherein Y is oxygen or sulfur and m and n independently of each other are an integer of from 1 to 3,
M is hydrogen or a metal selected from the group consisting of barium, nickel, manganese, calcium, zinc, iron, sodium, cobalt, tin, dialkyl tin, and
z has a value of from 1 to 4, the value of z being the same as the available valence of M.

Ramey et al U.S. Pat. Nos. 3,899,491, patented Aug. 12, 1975 and 3,920,659, patented Nov. 18, 1975, disclose alkyl alkanoate derivatives of substituted piperazines and substituted piperazinodiones. The substituted piperazines of U.S. Pat. No. 3,899,491 have the formula:

[structure: piperazine with $R^1$, $R^2$ substituents, H—N and N—$(CH_2)_m$C(H)($R^4$)—CO—$R^3$]

wherein
$R^1$ and $R^2$ are methyl or together with the carbon to which they are bound form a mono-cyclic ring system having five or six carbon atoms;
$R^3$ is an alkyl group of from one to twenty atoms;
$R^4$ is hydrogen or methyl, and
m is 0 or 1.

The substituted piperazinodiones of No. 3,920,659 have the formula:

[structure: piperazinodione with $R^1$, $R^2$ substituents, H—N and N—A—CO—$R^2$, subscript n]

wherein $R^1$ and $R^2$ are independently of each other methyl or ethyl or together with the carbon to which they are bound form a cyclopentyl or cyclohexyl ring, which is unsubstituted or substituted with a methyl group;

n is an integer of from 1 to 2;

when n is 1, $R^3$ is an alkyl group of from one to twenty carbon atoms;

when n is 2, $R^3$ is an alkylene group of from two to eight carbon atoms; and

A is a straight or branched chain (lower) alkylene group containing from one to six carbon atoms with the limitation that the terminals of said alkylene group bear only hydrogen or one (lower) alkyl group.

Ramey et al U.S. Pat. No. 3,920,661 patented Nov. 18, 1975 disclose dicarboxylic acids and salts in which one carboxylic acid group is esterified with a 2,2,6,6-tetrasubstituted-4-hydroxy piperidine and having the formula:

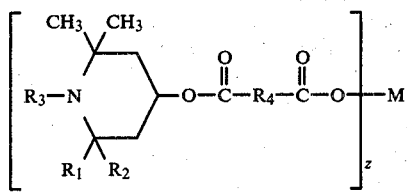

wherein $R_1$ and $R_2$ independently of each other are straight- or branched-chain alkyl having from one to six carbon atoms, or together with the carbon to which they are bound form a cyclopentyl or cyclohexyl ring, which is unsubstituted or substituted with a methyl group;

$R_3$ is hydrogen, alkyl having one to twelve carbon atoms, $\beta$-methoxyethyl, alkenyl having three or four carbon atoms, propargyl, benzyl or alkyl-substituted benzyl;

$R_4$ is straight or branched-chain alkylene having five to eight carbon atoms, or the group $(CH_2)_mY(CH_2)_n$ wherein Y is oxygen or sulfur and m and n independently of each other are an integer from 1 to 3;

M is hydrogen or a metal selected from the group consisting of barium, nickel, manganese, calcium, zinc, iron, sodium, cobalt, tin, and dialkyl tin, and z has a value of from 1 to 4, the value of z being the same as the available valence of M.

Ramey et al U.S. Pat. No. 3,939,163 patented Feb. 17, 1976 disclose closely similar compounds in which $R_4$ is alkylene having from one to four carbon atoms.

Randell et al U.S. Pat. No. 3,939,170 patented Feb. 17, 1976 disclose dehydropyridinyl sulphides, sulphoxides and sulphones having the formula:

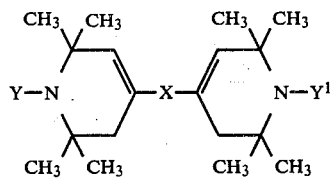

wherein

X is S, SO or $SO_2$ and Y and $Y^1$ are the same or different and each is H, OH, O— or a straight- or branched alkyl residue having from one to four carbon atoms, and salts thereof when Y and $Y^1$ are other than O—

Randell et al in published patent application No. B408,123 published Apr. 13, 1976 disclose substituted piperidine-4-ols having the formula:

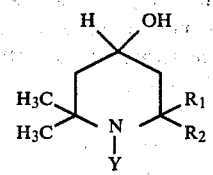

wherein $R_1$ and $R_2$ are the same or different and each is a straight- or branched alkyl residue having from one to twelve carbon atoms, or $R_1$ and $R_2$, together with the carbon atom to which they are attached, form a cycloalkyl residue having from five to twelve carbon atoms or the group:

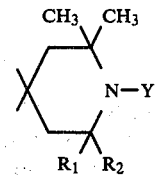

wherein $R_1$ and $R_2$ have their previous significance and Y is a straight- or branched alkyl residue having from one to twenty carbon atoms, an alkenyl or alkynyl residue having from three to twenty carbon atoms, an aralkyl residue having from seven to twelve carbon atoms or the group $—CH_2X$ wherein X is the group

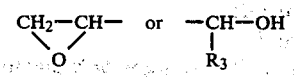

wherein $R_3$ is hydrogen, a methyl or phenyl residue, the group

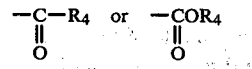

wherein $R_4$ is an alkyl residue having from one to twenty carbon atoms.

Cook U.S. Pat. No. 3,929,804 patented Dec. 30, 1975 discloses 4-piperidine acetamide compounds having the formula:

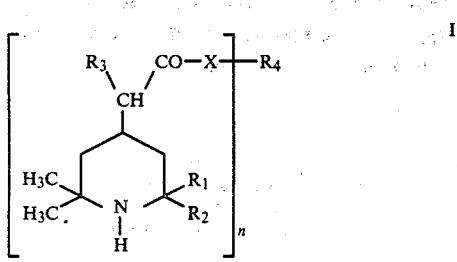

wherein
- R₁ and R₂ are the same or different and each is a straight- or branched alkyl residue having from one to twelve carbon atoms, or R₁ and R₂, together with the carbon atom to which they are attached form a cycloalkyl group having from five to twelve carbon atoms;
- R₃ is hydrogen, a straight- or branched alkyl residue having from one to four carbon atoms, an aralkyl residue having from seven to nine carbon atoms or a cycloalkyl group having from five or six carbon atoms;
- R₄ is a metal ion or a hydrocarbyl residue having from two to twenty carbon atoms and being either unsubstituted or substituted by halogen or interrupted by one or more oxygen or sulphur atoms;
- X is —O—, —S—, or >NR₅, wherein R₅ has the same significance as R₃; and
- n is 2, 3 or 4; as well as salts of the amine function of the compounds of formula I.

Cook U.S. Pat. No. 3,939,168 patented Feb. 17, 1976 discloses closely similar compounds having a Y substituent on the piperidyl nitrogen atom, Y being alkyl, alkenyl, aralkyl or a group

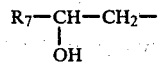

wherein
R₇ is hydrogen, alkyl or phenyl.

Randell et al U.S. Pat. No. 3,939,170, patented Feb. 17, 1976 provides di-4-(3,4-dehydro-2,2,6,6-tetramethyl piperidinyl) sulphides, sulphoxides and sulphones having the formula:

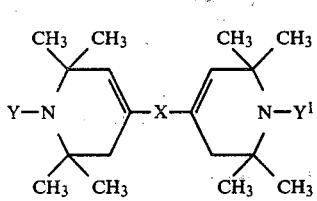

wherein
X is S, SO or SO₂ and Y and Y¹ are the same or different and each is H, OH, O· or a straight- or branched-alkyl residue having from one to four carbon atoms, and salts thereof when Y and Y¹ are other than O·.
Preferably X is S.

Smith et al U.S. Pat. No. 3,954,779, patented May 4, 1976 provides 4-(4'-hydroxycyclohexyl)2,2,6,6-tetramethyl piperidines and derivatives thereof having the formula:

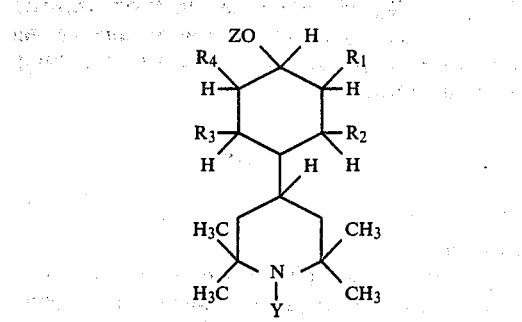

and salts thereof, wherein
- R₁, R₂, R₃ and R₄ are the same or different and each is hydrogen, an alkyl residue having from one to nine carbon atoms, a cycloalkyl residue having from five to fourteen carbon atoms or a cycloalkylalkyl residue having from seven to fourteen carbon atoms;
- Y is hydrogen;
- O an alkyl residue having from one to four carbon atoms, or an aralkyl residue having from seven to twelve carbon atoms; and
- Z is hydrogen, an unsubstituted or substituted alkyl residue having from one to twenty carbon atoms, an alkenyl or alkynyl residue having from two to twenty carbon atoms, a cycloalkyl residue having from five to twelve carbon atoms, an aralkyl residue having from seven to twelve carbon atoms, an aryl residue having from six to twelve carbon atoms, or the group having the formula:

—COZ₁ wherein
Z₁ has the same significance as Z as hereinbefore defined or Z₁ is a group —NR₅R₆ wherein
- R₅ is hydrogen or an alkyl residue having from one to four carbon atoms and
- R₆ is hydrogen, an alkyl residue having from one to twenty carbon atoms, a cycloalkyl residue having from five to twelve carbon atoms, an aralkyl residue having from seven to twelve carbon atoms or an aryl residue having from six to twelve carbon atoms.

Cook U.S. Pat. No. 3,959,291, patented May 25, 1976 provides derivatives of substituted 2-piperidinyl-4'-ethyl alcohol having the formula:

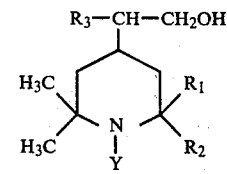

and salts thereof, wherein
- R₁ and R₂ are the same or different and each is an alkyl residue having from one to twelve carbon atoms, or R₁ and R₂, together with the carbon atom to which they are bound, form a cycloalkyl residue having from five to twelve carbon atoms in the ring;
- Y is O·, hydrogen, a straight- or branched-alkyl residue having from one to twenty carbon atoms, an alkenyl or alkynyl residue having from three to twelve carbon atoms, an aralkyl residue having from seven to twelve carbon atoms or a group having the formula:

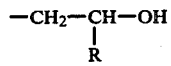

wherein
R is hydrogen, or a methyl or phenyl residue, and
$R_3$ is hydrogen, or a straight- or branched-chain alkyl residue having from one to twelve carbon atoms.

Cook U.S. Pat. No. 3,971,795, patented July 27, 1976 provides N-substituted piperidinylidene derivatives having the formula:

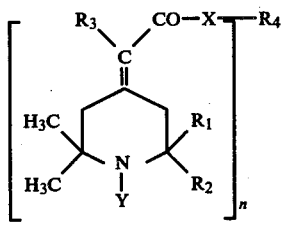

wherein
n is 1, 2, 3 or 4,
Y is hydrogen or a straight- or branched-alkyl residue having from one to twelve carbon atoms, an alkenyl residue having from three to twelve carbon atoms or an aralkyl residue having from seven to twelve carbon atoms and $R_1$ and $R_2$ are the same or different and each is a straight- or branched-alkyl residue having from one to twelve carbon atoms, or $R_1$ and $R_2$ together with the carbon atom to which they are attached form a cycloalkyl group having from five to twelve carbon atoms;
$R_3$ is hydrogen, a straight- or branched-alkyl residue having from one to four carbon atoms, an aralkyl residue having from seven to twelve carbon atoms, a cycloalkyl group having five or six carbon atoms;
$R_4$ is a hydrocarbyl residue having from one to twenty carbon atoms being either unsubstituted or substituted by halogen, or interrupted by one or more oxygen or sulphur atoms or $R_4$ is a metal ion, or, when n is 1, $R_4$, in addition, is hydrogen or has the structure:

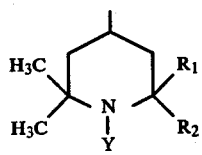

wherein
Y, $R_1$ and $R_2$ have their previous significance,
X is —O—, —S— or >$NR_5$
wherein
$R_5$ has the same significance as $R_3$ or when n is 1 in addition $R_5$ and $R_4$ together with the nitrogen atom to which they are bound form a heterocyclic residue having from four to ten carbon atoms;
as well as salts of the amine function of the compound of formula I.

Murayama et al U.S. Pat. No. 3,975,357, patented Aug. 17, 1976 provides 1-substituted piperidine derivatives having the formula:

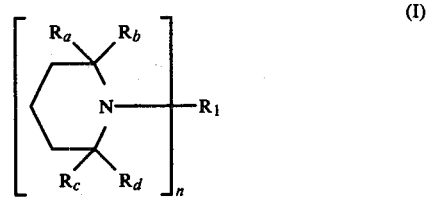

In the above formula, n represents 1 or 2.

$R_1$ represents when n=1, oxyl radical, hydroxy group, an alkyl group, a substituted alkyl group, an alkenyl group, an alkynyl group, an aralkyl group, a substituted aralkyl group or an acyl group, when n=2, an alkylene group (the alkylene chain may optionally be interrupted by an oxygen atom), 2-butenylene group, a group of the formula —CH$_2$COO—R$_7$—O—COCH$_2$— wherein $R_7$ represents an alkylene group or xylylene group, or a group of the formula —CH$_2$CH$_2$—O CO-(-R$_8$)$_{\overline{m}}$CO-O—CH$_2$CH$_2$— wherein m represents 0 or 1, $R_8$ represents an alkylene group (the alkylene chain may optionally be interrupted by a sulfur atom), an alkenylene group, phenylene group or 1,4-cyclohexylene group.

$R_a$ and $R_b$ represent methyl group or $R_a$ and $R_b$ together with carbon atom to which they are attached, form cyclohexyl group.

$R_c$ represents methyl group.

$R_d$ represents an alkyl group having one to five carbon atoms.

$R_c$ and $R_d$ together with carbon atom to which they are attached, may form cyclopentyl group, cyclohexyl group, a group of the formula:

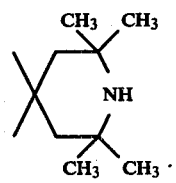

or a group of the formula

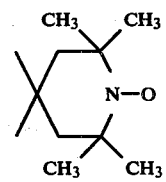

Marayama U.S. Pat. No. 3,975,462, patented Aug. 17, 1976 provides piperidine-spiro-hydantoin derivatives having the formula:

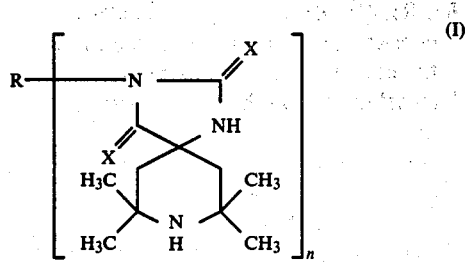

In the above formula (I), X represents oxygen atom or sulfur atom: n is an integer of 1 to 4 inclusive; and R represents when n is 1, an alkenyl group which may be substituted with halogen, an alkynyl group which may be substituted with phenyl, an aralkyl group which may be substituted with halogen, alkyl of one to four carbon atoms or halomethyl, a hydroxyalkyl group, an alkoxyalkyl group, an alkenyloxyalkyl group, an aryloxyalkyl group, an alkylthioalkyl group, an acyloxyalkyl group, an epoxyalkyl group, an N- alkyl-substituted aminoalkyl group, an alkoxycarbonyl alkyl group, an aryloxycarbonylalkyl group, an aliphatic acyl group, an alkoxycarbonyl group, a phosphino group which is substituted with phenoxy or alkoxy or a phosphinyl group which is substituted with phenoxy or alkoxy, when n is 2, an alkenylene group of four to eighteen carbon atoms, a dialkylene ether group, an aralkylene group, a bis-(acyloxyalkylene) group, or an alkylene-bis-(oxycarbonylalkyl)group, when n is 3, a tris-(acyloxyalkylene) group, an alkane-tris-(oxycarbonylalkyl) group or a group of the formula:

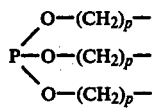

in which p is an integer of 1 to 8 inclusive and p's may be the same or different, and, when is 4, a tetrakis (acyloxyalkylene) group.

Ávár et al U.S. Pat. No. 3,976,658, patented Aug. 24, 1976 provides pyrazole derivatives of the formula:

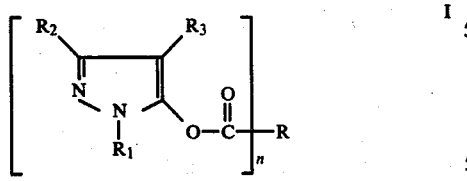

in which $R_1$ is a $C_{1-22}$ alkyl radical, a $C_{5-12}$ cycloalkyl radical, a $C_{6-12}$ cycloalkylalkyl radical, a $C_{7-12}$ aralkyl radical, of which the alkyl radical and the alkyl moiety of the cycloalkyl-alkyl radical are uninterrupted or interrupted by one or two sulphur atoms or by —COO—, and the aryl nucleus of the aralkyl radical is unsubstituted or substituted by a hydroxyl group and/or 1 or 2 $C_{1-12}$ alkyl radicals, or a phenyl group, unsubstituted or substituted by one or more substituents selected from one or two halogen atoms, a cyano group, a hydroxyl group, 1 or 2 $C_{1-12}$ alkyl radicals, 1 or 2 $C_{1-12}$ alkoxy radicals, a phenyl group and the radicals $R_4$—O— and $R_4$—$SO_2$—, wherein $R_4$ is a phenyl group, unsubstituted or substituted by 1 or 2 $C_{1-8}$ alkyl radicals, $R_2$, independently of $R_1$, has one of the significances of $R_1$, or is a cyano group or the radical —$COOR_5$, where $R_5$ is a $C_{1-12}$ alkyl radical, a $C_{5-12}$ cycloalkyl radical, a $C_{6-12}$ cycloalkyl-alkyl radical or a phenyl group, unsubstituted or substituted by a hydroxyl group and/or 1 or 2 $C_{1-8}$ alkyl radicals, $R_3$ is a hydrogen atom or one of the significances of $R_1$, —$COR_1$ or —$COOR_5$, n is 1, 2 or 3, and R, when n is 1, is a phenyl group, unsubstituted or substituted by a total of up to 3 substituents selected from 1 hydroxyl group, one to three halogen atoms, 1 phenyl group, 1 benzyl group, 1 phenoxy group, 1 to 3 alkyl radicals each containing one to eight carbon atoms and the sum of the carbon atoms not exceeding twelve, and 1 to 3 alkoxy radicals each containing one to twenty-two carbon atoms and the sum of the carbon atoms not exceeding twenty-two, or a monovalent naphthalene radical, or a monovalent radical of thiophene, benzothiophene, dibenzothiophene, furan, benzofuran, or dibenzofuran, and when n is 2, is a phenylene group, unsubstituted or substituted by a $C_{1-4}$ alkyl radical and/or a halogen atom, or a divalent naphthalene radical, or a divalent radical of thiophene or dibenzofuran, and when n is 3, is a 1,3,5-trivalent benzene radical.

Murayama et al, U.S. Pat. No. 4,061,616, patented Dec. 6, 1977, provides bipiperidyl derivatives having the following formula (I) or an acid addition salt thereof:

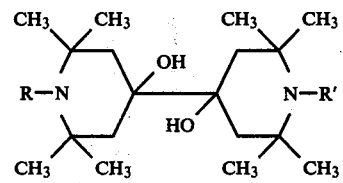

wherein

R and R', which may be the same or different, and each represents hydrogen atom, an alkyl group, an alkenyl group, an alkynyl group, an aralkyl group, a hydroxyalkyl group, an alkoxyalkyl group, an aliphatic or aromatic acyloxyalkyl group, a cyanoalkyl group, a halogenoalkyl group, an epoxyalkyl group, an alkoxycarbonylalkyl group, an aliphatic acyl group, an alkoxycarbonyl group or an aralkoxycarbonyl group.

Murayama U.S. Pat. No. 4,066,615 patented Jan. 3, 1978, provides stabilizers having the formula:

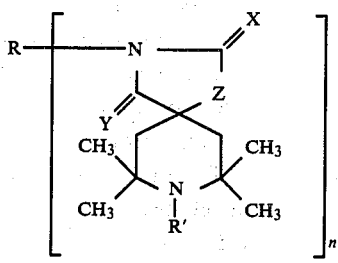

wherein:
R' represents an alkyl, an acyl, an alkoxycarbonyl, an amino or nitroso group;
X represents oxygen or sulfur;
Y represents oxygen, sulfur or a group of the formula =N—R'' in which R'' is hydrogen or alkyl;
Z represents oxygen or a group of the formula >N—R''' in which R''' is hydrogen or alkyl;
n is an integer of 1 to 4; and
R represents, when n is 1, alkyl, aryl, cycloalkyl, alkoxycarbonyl, substituted phosphino or substituted phosphinyl, when n is 2, alkylene, alkenylene, arylene, aralkylene; alkylenediphenylene, bis-(carboxycarbonyl) alkylene, alkylene-bis-(oxycarbonylalkyl), dialkylene ether or diphenylene ether, when n is 3, alkanetriyl, tris-(alkoxycarbonyl) alkanetriyl, alkanetriyl-tris-(oxycarbonylalkyl) or a group of the formula

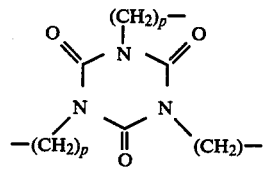

in which p is an integer of 1 through 8 inclusive, and, when n is 4, alkanetetrayl, tetrakis-(alkoxycarbonyl) alkanetetrayl or alkanetetrayl-tetrakis-(oxycarbonylalkyl).

In accordance with the instant invention, stabilizers for organic polymeric material are provided, comprising 2,2,6,6-tetraalkyl-4-piperidyl ketones and ketals having the general formula:

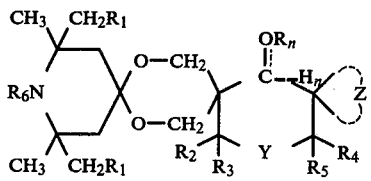

wherein:
n are each 0 or 1 and are each the same;
R is selected from the group consisting of hydrogen, alkyl having from one to about eighteen carbon atoms, and acyl

R' being alkyl having from one to about eighteen carbon atoms;

$R_1$, $R_2$, $R_3$, $R_4$ and $R_5$ are selected from the group consisting of hydrogen and alkyl having from one to about eighteen carbon atoms;
$R_6$ is selected from the group consisting of hydrogen and O·;
Y is selected from the group consisting of a carbon-to-carbon bond —, oxy —O—; alkylene having from one to about three carbon atoms, and alkyl-substituted alkylene, the alkylene having from one to about three carbon atoms, the alkyl having from one to about six carbon atoms; and
Z is selected from the group consisting of:

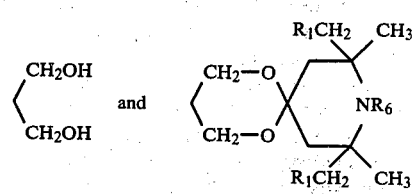

When each n is 0, and R and H are each missing, and the ketone carbonyl group

is present:

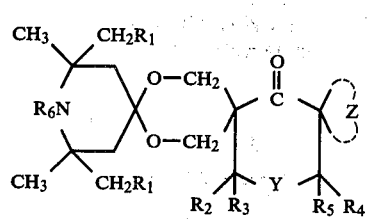

When each n is 1, and the compound is a ketal:

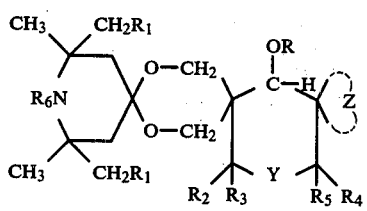

Exemplary R, $R_1$, $R_2$, $R_3$, $R_4$ and $R_5$ are methyl, ethyl, n-propyl, isopropyl, n-butyl, isobutyl, tertiary butyl, secondary butyl, n-amyl, isoamyl, tertiary amyl, n-hexyl, isohexyl, secondary hexyl, tertiary hexyl, heptyl, isoheptyl, octyl, tert-octyl, 2-ethyl hexyl, nonyl, decyl, undecyl, dodecyl, tridecyl, tetradecyl, hexadecyl, and octadecyl.

The alkylene radical has from one to three carbon atoms in a straight chain and from one to six alkyl groups having from one to six carbon atoms, selected from any of the above alkyl. Exemplary are methylene, ethylene, propylene, 1,3-butylene, 1,2-pentylene, 1,3-hexylene, 2,2-diethyl methylene and 2,3-diethyl propylene.

Examplary acyl

include formyl, acetyl, propionyl, butanoyl, octanoyl, 2-ethylhexanoyl, decanoyl, neodecanoyl, dodecanoyl, octadecanoyl, acrylyl, methacrylyl, crotonyl, linoleyl, phenylacetyl, cinnamyl, β-(3,5-di-t-butyl-4-hydroxyphenyl)propionyl, β-methylthiopropionyl, β-butylthiopropionyl, β-octylthiopropionyl, β-laurylthiopropionyl, β-stearylthiopropionyl, benzoyl, salicyloyl, p-t-butylbenzoyl, 3,5-di-t-butyl-4-hydroxybenzoyl, pyrrolidone carbonyl and nicotinoyl.

The ketone and ketal compounds indicated by the above general formulae are prepared by dehydrocondensation of alkyl-substituted piperidine-4-ones having the following general formula:

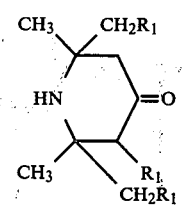

with bis-gem-tetramethyl cycloaliphatic and N-heterocyclic polyols such as 2,2,5,5-tetramethylol-cyclopentanone, 2,2,5,5-tetramethylol-cyclopentanol, 2,2,5,5-tetramethylol-3-methyl-cyclopentanol, 2,2,5,5-tetramethylol-3-butyl-cyclopentanol, 2,2,6,6-tetramethylol-cyclohexanone, 2,2,6,6-tetramethylol-3,3,5-trimethyl-cyclohexanol, 2,2,6,6-tetramethyl-4-ethylcyclohexanol, 2,2,6,6-tetramethylol-4-octylcyclohexanol, 2,2,7,7-tetramethylol-cycloheptanol, 2,2,8,8-tetramethylol-cyclooctanol, 3,3,5,5-tetramethylol-tetrahydropyran-4-one, and 3,3,5,5-tetramethylol-4-hydroxytetrahydropyran.

The following Example illustrates the preparation of the ketal compounds of the invention:

EXAMPLE I 2,2,6,6-Tetramethylol-cyclohexanol 5.5 g (0.025 mol) and 2,2,6,6-tetramethyl piperidine-4-one hydrochloride 10.5 g (0.055 mol) were dispersed in xylene 120 ml, and 0.5 g of p-toluene sulfonic acid added. The reaction mixture was refluxed under a water trap and condensed for five hours, while removing the water liberated in the water trap. After cooling, neutralization with 20% aqueous NaOH solution, and filtering the white precipitation produced, white crystals were obtained which were recrystallized from ethanol. Analysis of the compound gave the following results:

| M. p. | 240–242° C. | |
|---|---|---|
| Amine value | Theoretical | 5.67% |
| | Calculated | 5.65% |
| I.R. νOH | 3480 cm$^{-1}$ | |
| νNH | 3280 cm$^{-1}$ | |
| νC—O(ketal) | 1100 cm$^{-1}$ | |
| Elemental analysis: | C % H % N % | |
| Theoretical | 68.02 10.12 5.67 | |
| Calculated | 67.95 10.16 5.65 | |

The results showed the compound had the formula:

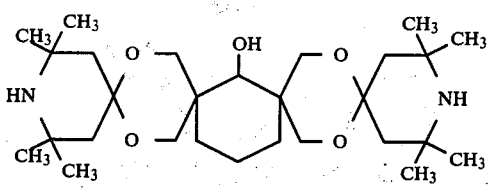

Using the above preparatory procedure, the following compounds have been prepared:

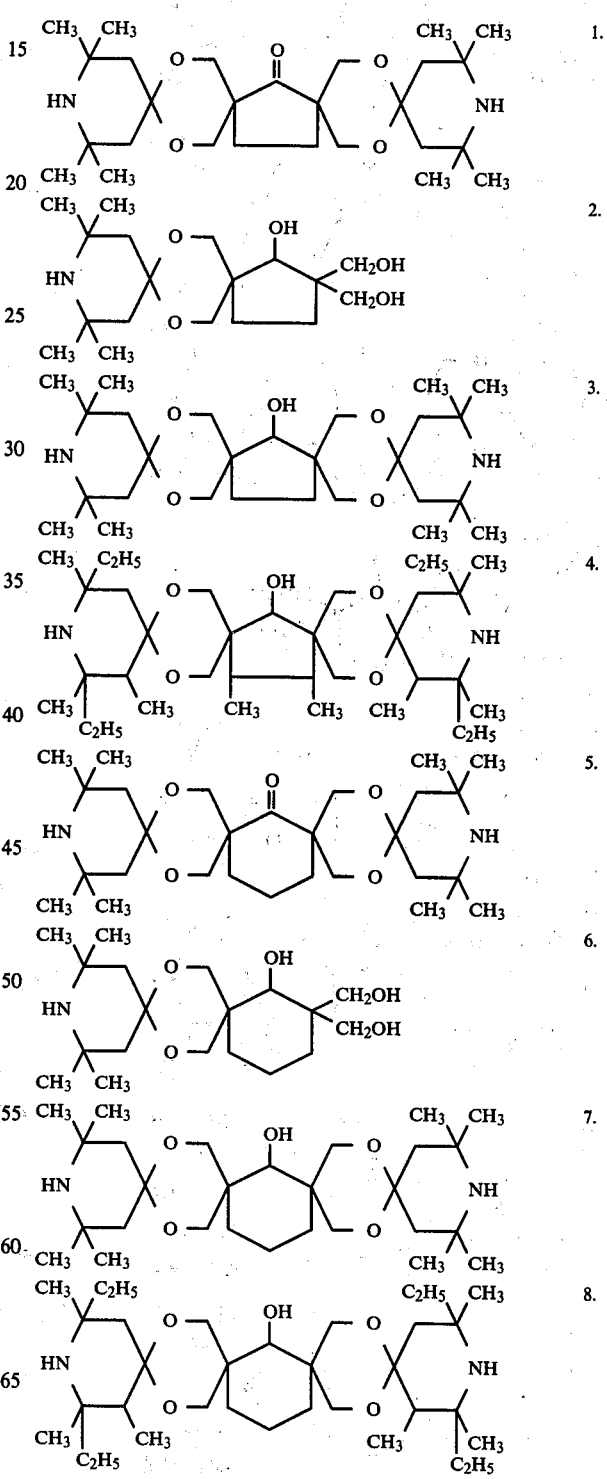

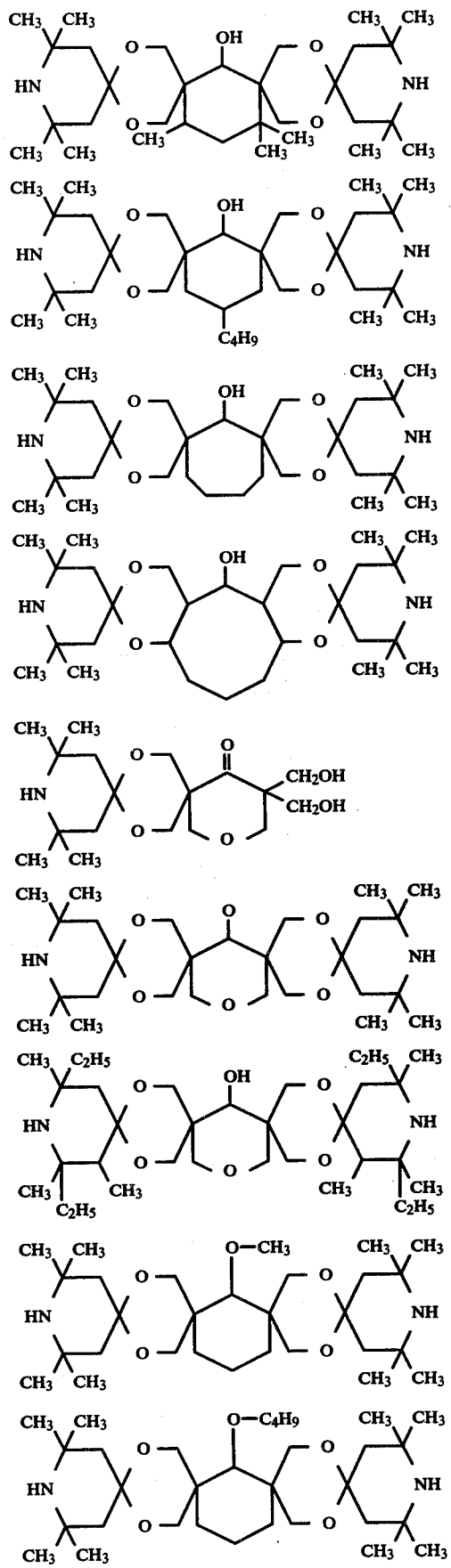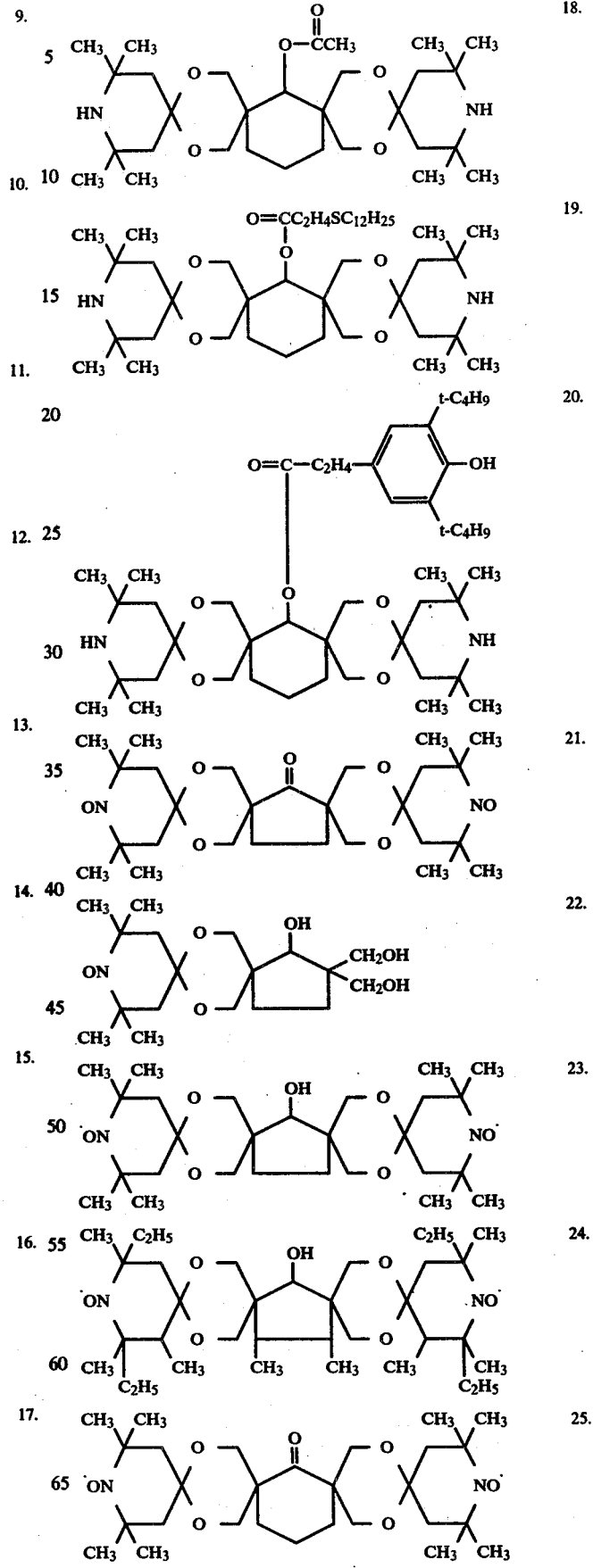

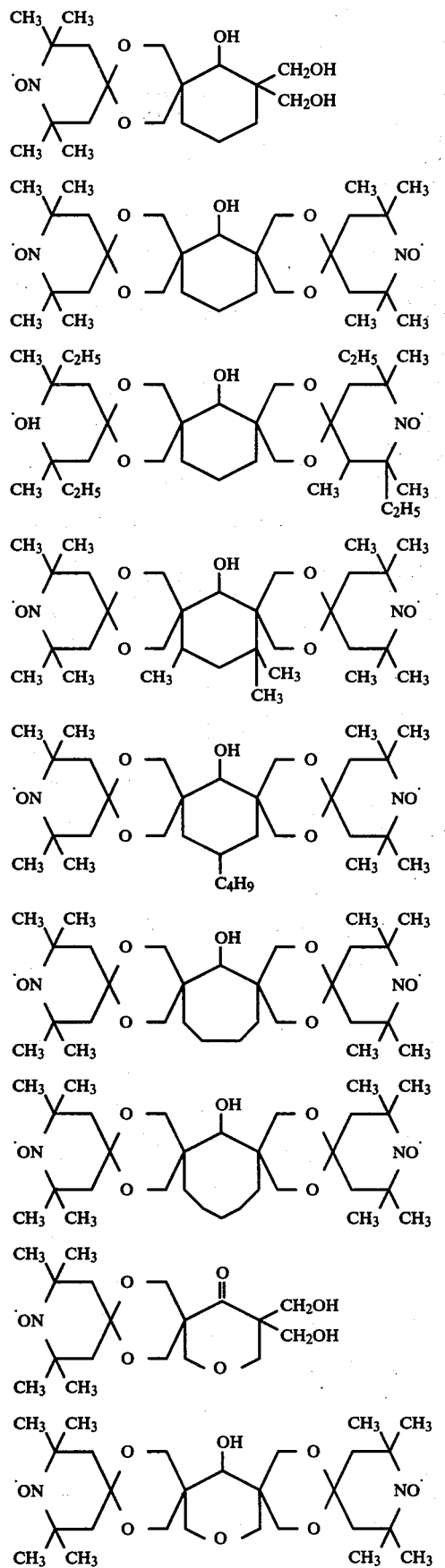
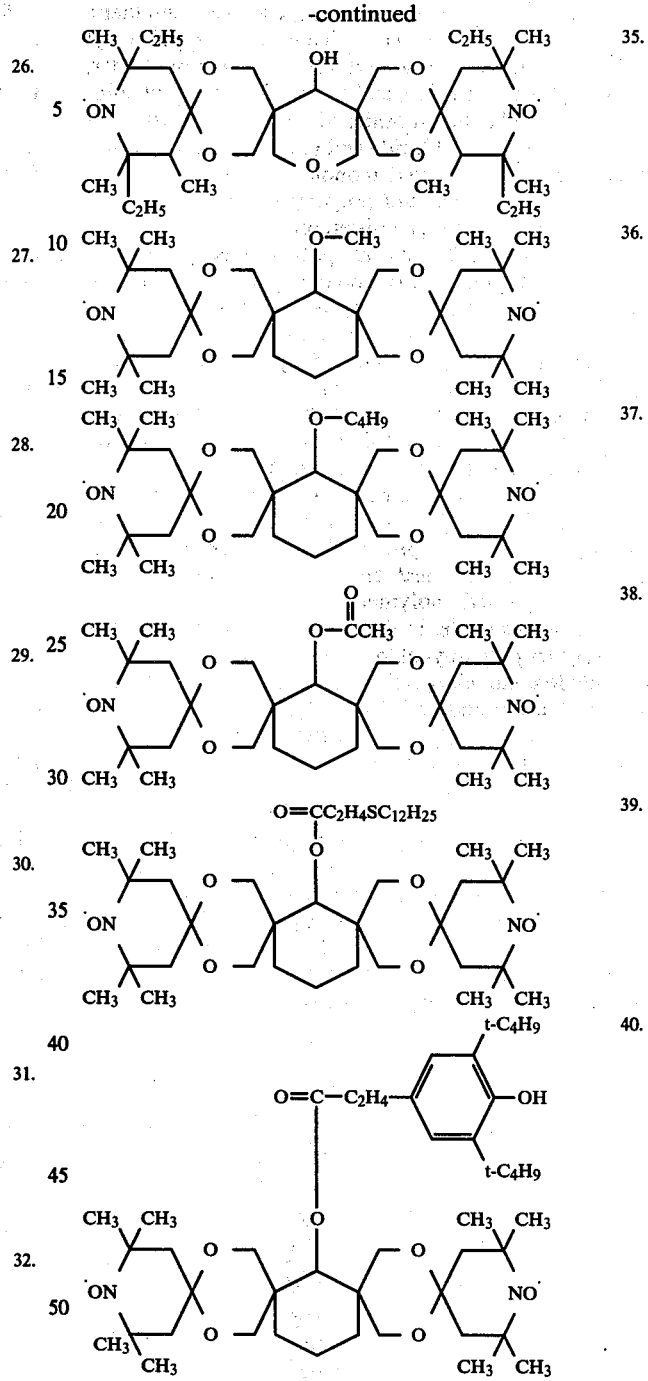

The 2,2,6,6-tetrasubstituted-4-piperidyl ketones and ketals of the invention are effective stabilizers to enhance the resistance to deterioration due to heat and/or light of synthetic polymeric materials which are susceptible to such degradation, including polyolefins such as low density polyethylene, high density polyethylene, polypropylene, polybutylene, polyisobutylene, polypentylene, and polyisopentylene; polystyrene; polydienes, such as polybutadiene and polyisoprene; and copolymers of olefins and dienes with other ethylenically and acetylenically unsaturated monomers, such as ethylene-propylene copolymers, ethylene-butene copolymers, ethylene-pentene copolymers, ethylenevinyl acetate copolymers, styrene-butadiene copolymers, acrylonitrile-styrenebutadiene copolymers, synthetic rubbers of all types, such as polychloroprene; polyvinyl halides; including polyvinyl chloride homopolymer; polyvinylidene chloride; and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycol-terephthalic acid ester polymers; polyamides such as polyepsiloncaprolactam; polyhexamethylene adipamide and polydecamethylene adipamide; polyurethanes; and epoxy resins.

The synthetic polymer can be in any physical form, including (for example) filaments, yarns, films, sheets, molded articles, latex, and foam.

The compounds of the invention can be used as a stabilizer in an amount within the range from about 0.01 to about 5 parts by weight, preferably from 0.05 to 3 parts by weight, per 100 parts by weight of resin.

The stabilizers of the invention can be employed as the sole stabilizer or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acids salts such as barium and cadmium salts of the higher fatty acids; organic triphosphites; organotin compounds; hindered phenols; and epoxy compounds.

With polyolefin resins there can be employed fatty acid salts of polyvalent metals, organic phoshites, phenolic and thiophenolic antioxidants, and the higher fatty alcohol esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile-butadiene-styrene terpolymers, antioxidants such as hindered phenols and bis-phenols, polvalent metal salts of the higher fatty acids, and organic phosphites can be used.

In addition, other conventional additives for synthetic polymers, such as plasticizers, lubricants, emulsifiers, antistatic agents, flameproofing agents, pigments and fillers, can be employed.

The following Examples in the opinion of the inventors represent preferred embodiments of synthetic resin compositions in accordance with the invention:

EXAMPLES 1 to 9

A group of polyvinyl chloride resin compositions was prepared having the following formulation:

| Ingredient | Parts by Weight |
| --- | --- |
| Polyvinyl chloride | 100 |
| Dioctylphthalate | 48 |
| Expoxidized soybean oil | 2.0 |
| Tris nonyl phenyl phosphite | 0.2 |
| Ca stearate | 1.0 |
| Zn stearate | 0.1 |
| Stablizer as shown in Table I | 0.2 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light.

This test was repeated for a total of nine stabilizers in accordance with the invention, having the formulae indicated in Table I, in comparison with two controls, 2-hydroxy-4-octoxy benzophenone, and 2,2,6,6-tetramethyl piperidinyl-4-benzoate. The following results were obtained:

TABLE I

| Example No. | Stabilizer | Hours to Failure |
| --- | --- | --- |
| Control 1 | None | 175 |
| Control 2 | 2-Hydroxy-4-octoxy-benzophenone | 330 |
| Control 3 | 2,2,6,6-Tetramethyl-piperidinyl-4-benzoate | 300 |
| 1 | [structure] | 515 |
| 2 | [structure] | 540 |
| 3 | [structure] | 520 |

TABLE I-continued

| Example No. | Stabilizer | Hours to Failure |
|---|---|---|
| 4 | 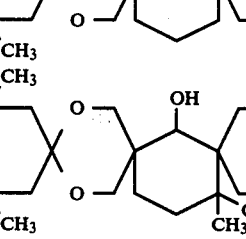 | 585 |
| 5 | 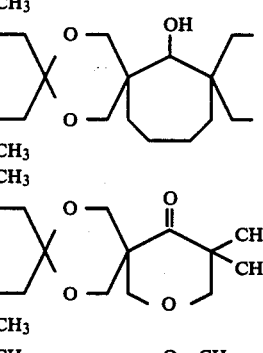 | 530 |
| 6 | 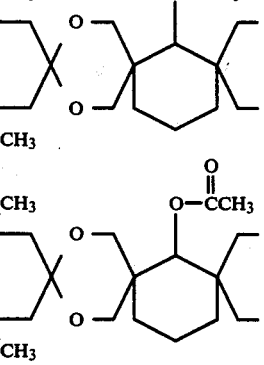 | 545 |
| 7 | 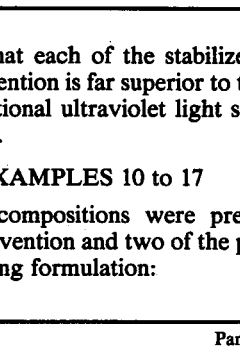 | 485 |
| 8 | 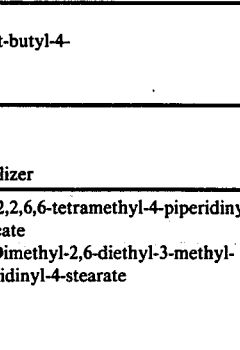 | 525 |
| 9 |  | 530 |

It is apparent that each of the stabilizers in accordance with the invention is far superior to the Controls, which are conventional ultraviolet light stabilizers for polyvinyl chloride.

EXAMPLES 10 to 17

Polypropylene compositions were prepared using stabilizers of the invention and two of the prior art, and having the following formulation:

| Ingredient | Parts by Weight |
|---|---|
| Polypropylene | 100 |
| Stearyl β-3,5-di-tert-butyl-4-hydroxyphenyl propionate | 0.2 |
| Stabilizer as shown in Table II | 0.3 |

The compositions were thoroughly blended in a Brabender Plastograph, and then compression-molded to form sheets 0.3 mm thick. The sheets were exposed to a high pressure mercury vapor lamp with and without immersion in hot water at 88° C. for 6 and 15 hours. The hours to failure were noted in comparison with two prior art stabilizers and the results are shown in Table II.

TABLE II

| | | Hours to Failure | | |
|---|---|---|---|---|
| Example No. | Stabilizer | Without Immersion | With Immersion for 6 hours | After Immersion for 15 hours |
| Control 1 | Bis-(2,2,6,6-tetramethyl-4-piperidinyl) sebacate | 490 | 415 | 325 |
| Control 2 | 2,6-Dimethyl-2,6-diethyl-3-methyl-piperidinyl-4-stearate | 265 | 230 | 180 |

TABLE II-continued
| Example No. | Stabilizer | Hours to Failure | | |
|---|---|---|---|---|
| | | Without Immersion | With Immersion for 6 hours | After Immersion for 15 hours |
| 10 | 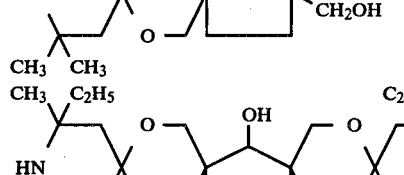 | 625 | 570 | 505 |
| 11 | 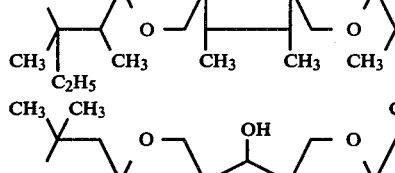 | 640 | 595 | 540 |
| 12 | 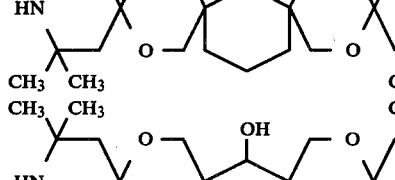 | 715 | 685 | 645 |
| 13 | 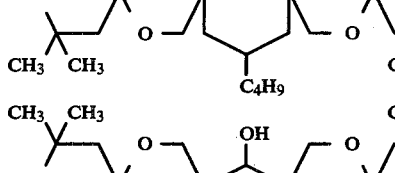 | 665 | 625 | 565 |
| 14 | 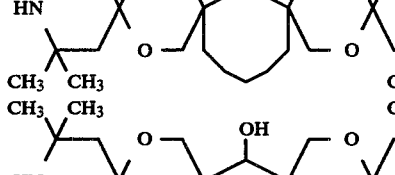 | 650 | 600 | 545 |
| 15 | 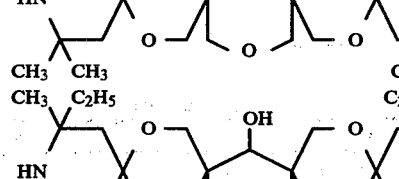 | 680 | 645 | 600 |
| 16 | 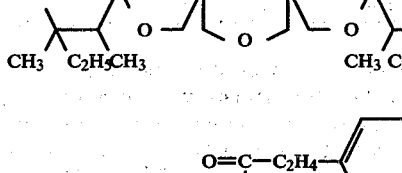 | 655 | 615 | 565 |
| 17 | 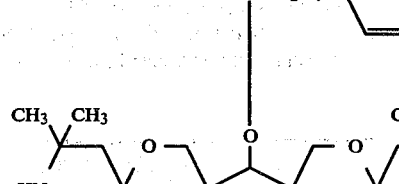 | 685 | 645 | 595 |

It is apparent from the above results that the compounds of the invention are superior stabilizers in enhancing the resistance of the polypropylene polymer composition to deterioration in the presence of ultraviolet light.

EXAMPLES 18 to 26

Ethylene-vinyl acetate copolymer compositions were prepared using stabilizers of the invention and two of the prior art, and having the following formulation:

| Ingredient | Parts by Weight |
|---|---|
| Ethylene-vinylacetate copolymer | 100 |
| 2,6-di-t-butyl-p-cresol | 0.1 |
| Ca-stearate | 0.1 |
| Zn-stearate | 0.1 |
| Diisodecylphenylphosphite | 0.2 |
| Stabilizer as shown in Table III | 0.3 |

The stabilizer was blended with the polymer on a two-roll mill at 130° C., and sheets 0.4 mm thick were then compression-molded at 140° C. from the resulting blend. Pieces 2.5 cm square were cut off from the sheets and exposed to ultraviolet light in a Weather-O-Meter for 500 hours. At the start and at the conclusion of the test, tensile strength of the sheet samples was determined. The results in comparison with two controls, 2-hydroxy-4-methoxy benzophenone and 2-(2'-hydroxy-5'-chlorophenyl) benzotriazole, are given in Table III at % retention of the initially determined tensile strength:

TABLE III

| Example No. | Stabilizer | % Retention of Tensile Strength after 500 Hours |
|---|---|---|
| Control 1 | 2-Hydroxy-methoxy-benzophenone | 70 |
| Control 2 | 2-(2'-Hydroxy-5'-chlorophenyl) benzotriazole | 73 |
| 18 | [structure] | 81 |
| 19 | [structure] | 84 |
| 20 | [structure] | 83 |
| 21 | [structure] | 88 |
| 22 | [structure] | 82 |
| 23 | [structure] | 86 |

TABLE III-continued

| Example No. | Stabilizer | % Retention of Tensile Strength after 500 Hours |
|---|---|---|
| 24 | [structure: two 2,2,6,6-tetramethylpiperidine units linked via spiro ketal to central cyclohexane ring bearing OH] | 84 |
| 25 | [structure: two 2,2,6,6-tetramethylpiperidine units linked via spiro ketal to central cyclohexane ring bearing O—C$_4$H$_9$] | 83 |
| 26 | [structure: two 2,2,6,6-tetramethylpiperidine units linked via spiro ketal to central cyclohexane ring bearing O—C(=O)C$_2$H$_4$SC$_{12}$H$_{25}$] | 82 |

It is apparent from the results that the stabilizer compsitions in accordance with the invention are superior to the controls in enhancing the resistance of the ethylene-vinyl acetate copolymer to deterioration in the presence of ultraviolet light.

EXAMPLES 27 to 36

High density polyethylene compositions were prepared using the stabilizers of the invention and two of the prior art, and having the following formulation:

| Ingredient | Parts by Weight |
|---|---|
| High-density polyethylene | 100 |
| Ca-stearate | 1.0 |
| Tetrakis (methylene-3-(3,5-di-t-butyl-4-hydroxyphenyl)propionate)methane | 0.1 |
| Distearylthiodipropionate | 0.3 |
| Stabilizer as shown in Table IV | 0.3 |

The stabilizer was blended with the polymer on a two-roll mill and sheets 0.5 mm thick were prepared by compression-molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table IV:

TABLE IV

| Example No. | Stabilizer | Hours to Failure |
|---|---|---|
| Control 1 | 2-(2'-Hydroxy-5'-methylphenyl)benzotriazole | 740 |
| Control 2 | 2,2,6,6-Tetramethyl-4-piperidinyl acetate | 490 |
| 27 | [structure: 2,2,6,6-tetramethylpiperidine linked via spiro ketal to cyclopentane ring bearing OH, CH$_2$OH, CH$_2$OH] | 1230 |
| 28 | [structure: two 2,2,6,6-tetramethylpiperidine units linked via spiro ketal to central ring bearing OH] | 1370 |
| 29 | [structure: two 2,2,6,6-tetramethylpiperidine units linked via spiro ketal to central ring bearing C=O] | 1280 |

TABLE IV-continued

| Example No. | Stabilizer | Hours to Failure |
|---|---|---|
| 30 | [structure] | 1450 |
| 31 | [structure] | 1340 |
| 32 | [structure] | 1300 |
| 33 | [structure] | 1350 |
| 34 | [structure] | 1320 |
| 35 | [structure] | 1300 |
| 36 | [structure] | 1340 |

The stabilizers of the invention are clearly superior to the controls in enhancing resistance of the polyethylene to degradation under ultraviolet light.

EXAMPLES 37 to 45

Five acrylonitrile-butadiene-styrene terpolymer resin compositions were prepared using stabilizers of the invention and two of the prior art, and having the following formulation:

| Ingredient | Parts by Weight |
|---|---|
| Acrylonitrile-butadiene-styrene terpolymer | 100 |
| 4,4'-butylidene-bis-(2-tert-butyl-m-cresol) | 0.1 |

| Ingredient | Parts by Weight |
|---|---|
| Stabilizer as shown in Table V | 0.3 |

The stabilizer was blended with the resin on a two-roll mill, and sheets 3 mm thick were prepared by compression molding of the resulting blend. Pieces 2.5 cm square were cut off from the sheets, and subjected to ultraviolet light in a Weather-O-Meter for 800 hours. Tensile strength before and after the test exposure was determined, and the results reported as the percent of tensile strength retained, at the end of this time, in Table V.

TABLE V

| Example No. | Stabilizer | % Tensile Strength Retained |
|---|---|---|
| Control 1 | 2,4-Dihydroxy benzophenone | 55 |
| Control 2 | 2,4-Di-t-butylphenyl-3,5-di-t-butyl-4-hydroxy benzoate | 49 |
| 37 | [structure] | 89 |
| 38 | [structure] | 86 |
| 39 | [structure] | 83 |
| 40 | [structure] | 92 |
| 41 | [structure] | 86 |
| 42 | [structure] | 85 |
| 43 | [structure] | 88 |
| 44 | [structure] | 87 |

TABLE V-continued

| Example No. | Stabilizer | % Tensile Strength Retained |
|---|---|---|
| 45 | [structure: bis-hindered amine spiro compound with O=CC₂H₄SC₁₂H₂₅ ester group on cyclohexane core] | 85 |

It is apparent from the data that the stabilizers of the invention are superior to the stabilizers of the prior art.

EXAMPLES 46 to 52

Polybutylene terephthalate resin formulations were prepared having the following composition:

| Ingredient | Parts by Weight |
|---|---|
| Polybutylene terephthalate | 100 |
| 1,3,5-trimethyl-2,4,6-tris (3,5-di-t-butyl-4-hydroxybenzyl) benzene | 0.1 |
| Stabilizer as shown in Table VI | 0.2 |

The compositions were extruded to form pellets, and then test pieces were molded from the pellets by injection molding at 270° C. The test pieces were irradiated with ultraviolet light for 500 hours in a Weather-O-Meter. Tensile strength before and after exposure was determined, and the percent tensile strength retained after the exposure is given in Table VI.

TABLE VI

| Example No. | Stabilizer | % Retention of Tensile Strength |
|---|---|---|
| Control 1 | 9-Aza-8,8,10,10-tetramethyl-3-ethyl-3-hydroxymethyl-1,5-dioxaspiro [5,5] undecane | 43 |
| Control 2 | 2-Hydroxy-4-octoxy-benzophenone | 52 |
| 46 | [structure with cyclopentane central ring, OH substituent, flanked by two tetramethyl-piperidine dioxaspiro groups] | 87 |
| 47 | [structure with cyclohexane central ring, OH substituent, flanked by two tetramethyl-piperidine dioxaspiro groups] | 91 |
| 48 | [structure with cycloheptane central ring, OH substituent, flanked by two tetramethyl-piperidine dioxaspiro groups] | 88 |
| 49 | [structure with cyclooctane central ring, OH substituent, flanked by two tetramethyl-piperidine dioxaspiro groups] | 85 |
| 50 | [structure with central ring bearing OH and additional O substituents, flanked by two tetramethyl-piperidine dioxaspiro groups] | 88 |

TABLE VI-continued

| Example No. | Stabilizer | % Retention of Tensile Strength |
|---|---|---|
| 51 | [chemical structure] | 87 |
| 52 | [chemical structure] | 89 |

It is apparent that the stabilizers of the invention are effective ultraviolet light stabilizers for polybutylene terephthalate resins.

EXAMPLES 53 to 60

Polyurethane resin compositions were prepared using stabilizers of the invention and having the following formulation:

| Ingredient | Parts by Weight |
|---|---|
| Polyurethane resin (Asahidenka Kogyo, U-100)[1] | 100 |
| Ba-stearate | 0.7 |
| Zn-stearate | 0.3 |
| 2,6,di-t-butyl-p-cresol | 0.1 |
| Stabilizer as shown in Table VII | 0.3 |

[1] A polyurethane-isocyanurate made from toluene diisocyanate and alkylene polyol.

The stabilizer was blended with the finely powdered polyurethane resin on a two-roll mill for five minutes at 70° C., and the sheet was then compression-molded at 120° C. for five minutes to form sheets 0.5 mm thick. The sheets were exposed to ultraviolet light in a Weather-O-Meter for thirty hours. The elongation was noted at the beginning and at the conclusion of the test period, and the results are given in Table VII as % elongation retention.

TABLE VII

| Example No. | Stabilizer | % Elongation Retention |
|---|---|---|
| Control | 2-Hydroxy-4-methoxy-benzophenone | 55 |
| 53 | [chemical structure] | 75 |
| 54 | [chemical structure] | 72 |
| 55 | [chemical structure] | 81 |

TABLE VII-continued

| Example No. | Stabilizer | % Elongation Retention |
|---|---|---|
| 56 | 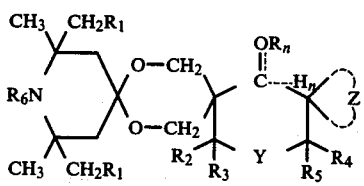 (structure) | 73 |
| 57 | (structure) | 77 |
| 58 | (structure) | 69 |
| 59 | (structure) | 78 |
| 60 | (structure) | 76 |

The stabilizers of the invention are clearly superior to the control in enhancing resistance of the polyurethane resin to degradation under ultraviolet light.

Having regard to the foregoing disclosure, the following is claimed as the inventive and patentable embodiments thereof:

1. 2,2,6,6-tetraalkyl-4-piperidyl ketones and ketals having the formula:

wherein:

n are each 0 or 1 and are each the same;

R is selected from the group consisting of hydrogen, alkyl having from one to about eighteen carbon atoms, and acyl $$R'C-,$$
$$\|$$
$$O$$

R' being selected from the group consisting of alkyl and alkenyl having from one to about eighteen carbon atoms, and such radicals containing phenyl, thioalkyl and phenolic groups, pyrrolidonyl and nicotinyl;

$R_1$, $R_2$, $R_3$, $R_4$ and $R_5$ are selected from the group consisting of hydrogen and alkyl having from one to about eighteen carbon atoms;

$R_6$ is selected from the group consisting of hydrogen and O·;

Y is selected from the group consisting of a carbon-to-carbon bond —, oxy —O—; alkylene having from one to about three carbon atoms, and alkyl-substituted alkylene, the alkylene having from one to about three carbon atoms, the alkyl having from one to about six carbon atoms; and Z is selected from the group consisting of:

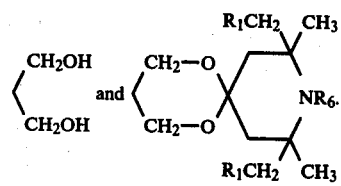

2. A compound according to claim 1 in which R is hydrogen.

3. A compound according to claim 1 in which R is alkyl.

4. A compound according to claim 1 in which R is acyl

5. A compound according to claim 1 in which $R_6$ is hydrogen.

6. A compound according to claim 1 in which $R_6$ is O·.

7. A compound according to claim 1 in which one of $R_1$, $R_2$, $R_3$, $R_4$ and $R_5$ is alkyl.

8. A compound according to claim 1 in which all of $R_1$, $R_2$, $R_3$, $R_4$ and $R_5$ are hydrogen.

9. A compound according to claim 1 in which Y is a carbon-to-carbon bond—.

10. A compound according to claim 1 in which Y is oxy —O—.

11. A compound according to claim 1 in which Y is alkylene having from one to about three carbon atoms.

12. A compound according to claim 1 in which Y is alkyl-substituted alkylene, the alkylene having from one to about three carbon atoms, and the alkyl having from about one to about six carbon atoms.

13. A compound according to claim 1 in which Z is

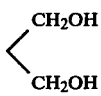

14. A compound according to claim 12 in which Z is

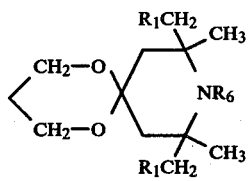

15. A compound according to claim 1 having the formula:

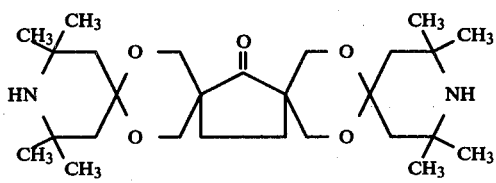

16. A compound according to claim 1 having the formula:

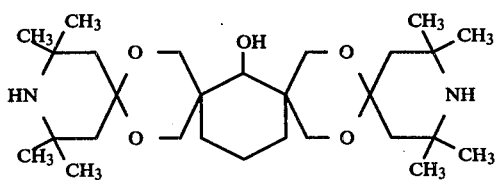

17. A compound according to claim 1 having the formula:

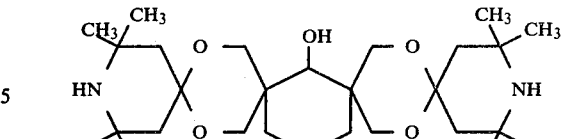

18. A compound according to claim 1 having the formula:

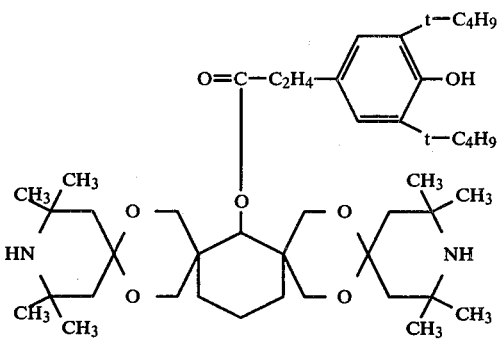

19. A compound according to claim 1 having the formula:

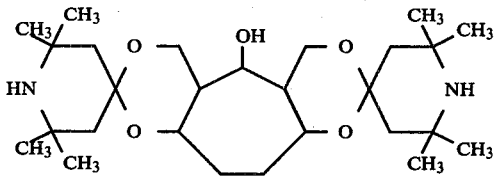

20. A polyvinyl chloride resin composition having improved resistance to deterioration when heated at 350° F., comprising a polyvinyl chloride resin and a compound in accordance with claim 1.

21. A polyvinyl chloride resin composition in accordance with claim 20, in which the polyvinyl chloride resin is polyvinyl chloride homopolymer.

22. A polyvinyl chloride resin composition in accordance with claim 20, in which the polyvinyl chloride resin is a copolymer of vinyl chloride and vinyl acetate.

23. An olefin polymer composition having improved resistance to deterioration comprising an olefin polymer selected from the group consisting of polymers of alpha-olefins having from two to six carbon atoms and polystyrene, and a compound in accordance with claim 1.

24. An olefin polymer composition in accordance with claim 23 wherein the polyolefin is polypropylene.

25. An olefin polymer composition in accordance with claim 23 wherein the polyolefin is polyethylene.

26. An acrylonitrile-butadiene-styrene polymer having its resistance to deterioration when heated at 300° F. and above enhanced by a compound in accordance with claim 1.

27. A polyester polymer composition having improved resistance to deterioration comprising a linear polyester polymer and a compound in accordance with claim 1.

28. A polyurethane resin composition having improved resistance to deterioration comprising a polyurethane resin and a compound in accordance with claim 1.

29. An ethylene-vinyl acetate copolymer composition having improved resistance to deterioration comprising an ethylene-vinyl acetate copolymer and a compound in accordance with claim 1.

* * * * *

UNITED STATES PATENT AND TRADEMARK OFFICE
CERTIFICATE OF CORRECTION

PATENT NO. : 4,173,599
DATED : November 6, 1979
INVENTOR(S) : Motonobu Minagawa et al It is certified that error appears in the above-identified patent and that said Letters Patent are hereby corrected as shown below:

Column 7, line 28 :

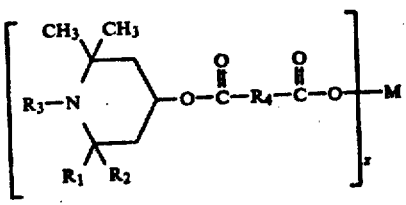

should be

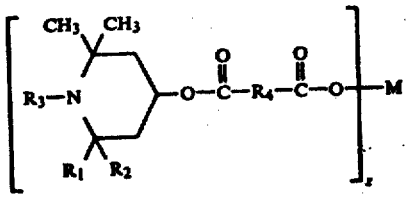

Column 8, line 4 : "O-" should be --O-.--

Column 9, line 10 :

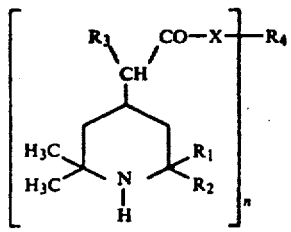   should be   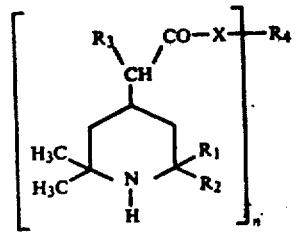

UNITED STATES PATENT AND TRADEMARK OFFICE
CERTIFICATE OF CORRECTION

PATENT NO. : 4,173,599
DATED : November 6, 1979
INVENTOR(S) : Motonobu Minagawa et al It is certified that error appears in the above-identified patent and that said Letters Patent are hereby corrected as shown below:

Column 9, line 60 : "O·" should be --O˙--.
Column 9, line 63 : "O·" should be --O˙--.
Column 10, line 23 : after "O" please insert --is--.
Column 10, line 67 : "O" should be --O˙--.
Column 11, line 17 :

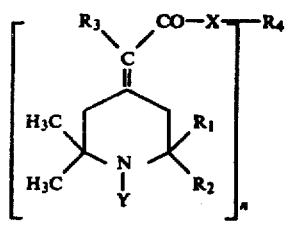   should be   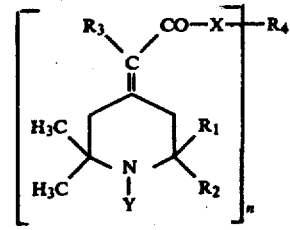

Column 11, line 60 : "O" should be --O˙--.
Column 12, line 65 : "Marayama" should be --Murayama--.
Column 13, line 45 : after "when" please insert --n--.
Column 15, line 35 :

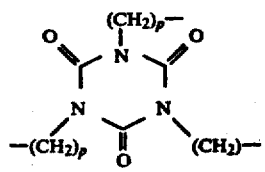   should be   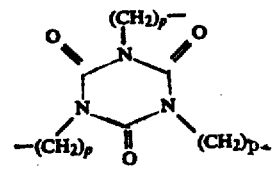

UNITED STATES PATENT AND TRADEMARK OFFICE
CERTIFICATE OF CORRECTION

PATENT NO. : 4,173,599

DATED : November 6, 1979

INVENTOR(S) : Motonobu Minagawa et al

It is certified that error appears in the above-identified patent and that said Letters Patent are hereby corrected as shown below:

Column 15, line 50 :

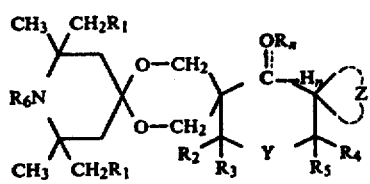 should be 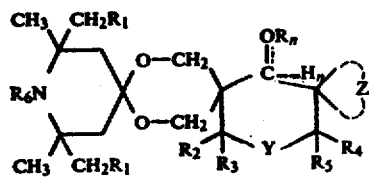

Column 16, line 50 :

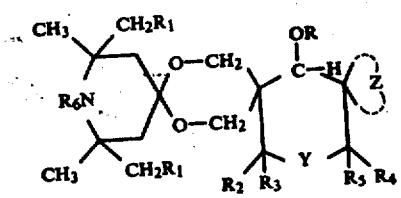 should be 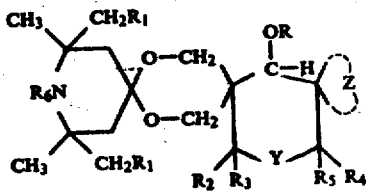

Column 16, line 68 : "Examplary" should be --Exemplary--

UNITED STATES PATENT AND TRADEMARK OFFICE
CERTIFICATE OF CORRECTION

PATENT NO. : 4,173,599
DATED : November 6, 1979
INVENTOR(S) : Motonobu Minagawa et al It is certified that error appears in the above-identified patent and that said Letters Patent are hereby corrected as shown below:

Column 20, Formula 21:

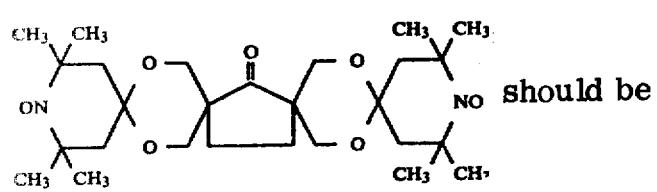 should be 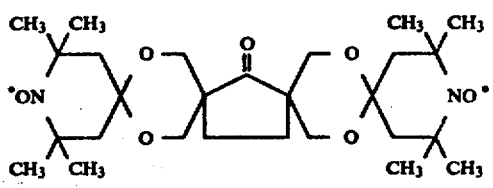

Column 20, Formula 22:

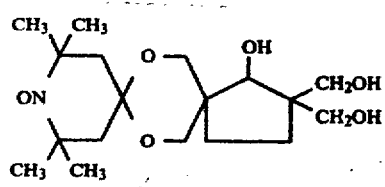 should be 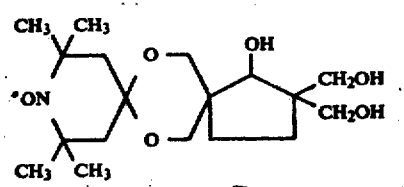

UNITED STATES PATENT AND TRADEMARK OFFICE
CERTIFICATE OF CORRECTION

PATENT NO. : 4,173,599
DATED : November 6, 1979
INVENTOR(S) : Motonobu Minagawa et al It is certified that error appears in the above-identified patent and that said Letters Patent are hereby corrected as shown below:

Column 23, line 31 : "phoshites" should be --phosphites--.
Column 24, line 21 : "Expoxidized" should be --Epoxidized--.
Column 27, Formula 14 :

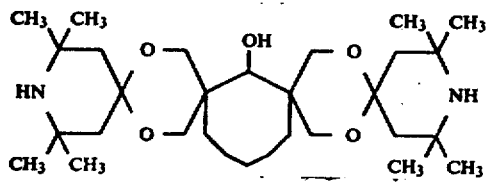 should be 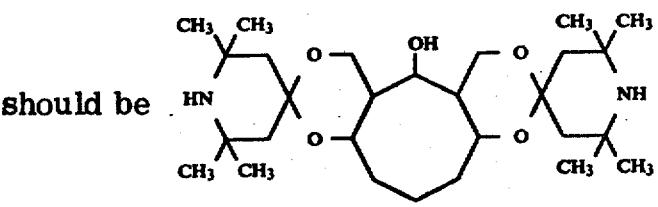

Column 30, line 16 : "at" should be --as--
Column 41, Claim 1
Formula

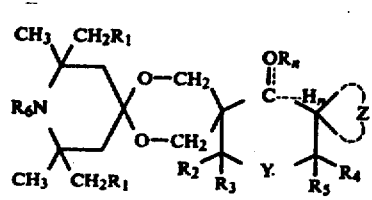 should be 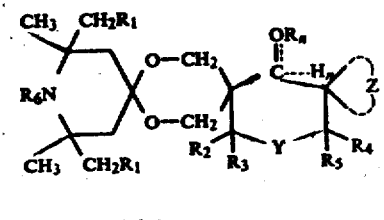

Column 42, line 68 : after "acyl" please insert --R'C-  --.
O

UNITED STATES PATENT AND TRADEMARK OFFICE
CERTIFICATE OF CORRECTION

PATENT NO. : 4,173,599
DATED : November 6, 1979
INVENTOR(S) : Motonobu Minagawa et al It is certified that error appears in the above-identified patent and that said Letters Patent are hereby corrected as shown below:

Column 44, line 33 :

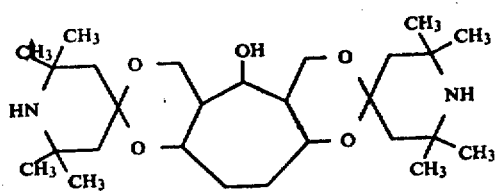 should be 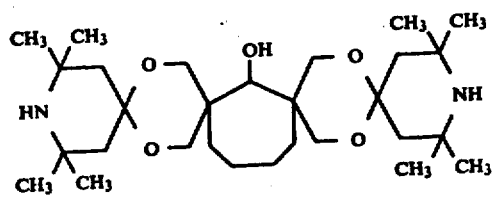

Signed and Sealed this

Twenty-fifth Day of March 1980

[SEAL]

Attest:

SIDNEY A. DIAMOND

Attesting Officer

Commissioner of Patents and Trademarks